United States Patent [19]

Wrathall et al.

[11] Patent Number: 5,412,075
[45] Date of Patent: May 2, 1995

[54] CONTROL OF METHIONINE CONTENT IN PHOTOGRAPHIC GRADE GELATIN

[75] Inventors: Donald P. Wrathall, Topsfield, Mass.; John E. Keevert, Jr.; Gregg C. Hider, both of Rochester, N.Y.; John S. Brand, Pittsford, N.Y.

[73] Assignee: Eastman Kodak Company, Rochester, N.Y.

[21] Appl. No.: 227,171

[22] Filed: Apr. 13, 1994

Related U.S. Application Data

[63] Continuation of Ser. No. 849,483, Mar. 11, 1992, abandoned.

[51] Int. Cl.$^6$ .......................... C07K 4/12; G03C 1/047
[52] U.S. Cl. ..................................... 530/355; 530/354; 530/840; 430/642
[58] Field of Search ....................... 530/355, 354, 840; 430/642

[56] References Cited

U.S. PATENT DOCUMENTS

| | | | |
|---|---|---|---|
| 1,289,053 | 12/1918 | Mumford | 530/355 |
| 1,613,362 | 1/1927 | Sheppard et al. | 530/355 |
| 2,191,206 | 9/1937 | Schwartz | 430/642 |
| 4,315,072 | 2/1982 | Fox et al. | 430/628 |
| 4,713,320 | 12/1987 | Maskasky | 430/567 |
| 4,914,014 | 4/1990 | Daubendiek et al. | 430/569 |
| 4,992,362 | 2/1991 | Moll et al. | 430/569 |

FOREIGN PATENT DOCUMENTS

| | | |
|---|---|---|
| 0423840 | 4/1991 | European Pat. Off. |
| 0024135 | of 1914 | United Kingdom |
| 0245456 | 6/1925 | United Kingdom |

OTHER PUBLICATIONS

Joe E. Maskasky "A Comparison of Oxidized and Non-Oxidized Gelatins. I. Silver Ion Binding" *J. Imag. Sci.* 33(1), 10–13, (Jan./Feb., 1989).

Joe E. Maskasky "A Comparison of Oxidized and Non-Oxidized Gelatins. II. Precipiation of Tabular Grain Emulsions" *J. Imag. Sci.* 33(1), 13–17 (Jan./Feb., 1989).

J. Pouradier and A. Rondeau "On the MethionineSulphoxide of Gelatin" *J. Photo. Sci.* 16, 68–69 (1968).

F. Moll "Investigations on Oxidized Gelatins" *J. Photo. Sci.* 34, 47–52 (1986).

S. Tani and T. Tani "Simultaneous Determination of Methionine and Its Oxides in Gelatin" informal meetings abstract from Soc. of Photographic Sciences and Technology of Japan, Nov. 21–22, 1991 issued to attendees.

F. Moll "The Oxidation of Gelatin" *J. Photo. Sci.* 37, 14–18 (1989).

R. Hayashi and F. Suzuki "Determination of Methionine Sulfoxide in Protein and Food by Hydrolysis with p-Toluenesulfonic Acid" *Anal. Chem.* 149, 521–528 (1985).

Simpson et al. "Complete Amino Acid Analysis of Proteins from a Single Hydrolysate" *J. Bio. Chem.* 251(7), 1936–1940 (Apr., 1976).

*Primary Examiner*—William H. Beisner
*Assistant Examiner*—C. Sayala
*Attorney, Agent, or Firm*—Alfred P. Lorenzo

[57] ABSTRACT

The method for preparing high grade gelatin with a specific methionine content and with reduced methionine variability from batch to batch and within a single extraction includes controlling the amount of and variability of oxidant present during processing of bone stock into gelatin. Such controls include control of oxidant concentration and range in process water, control of volume of process water used in gelatin-making process and restriction of the range of gelatin extracts used in the product gelatin. Once the aim level of oxidant has been set, the total range of oxidant around the set point should be less than 220 meq per 100 kg dry bone.

5 Claims, 3 Drawing Sheets

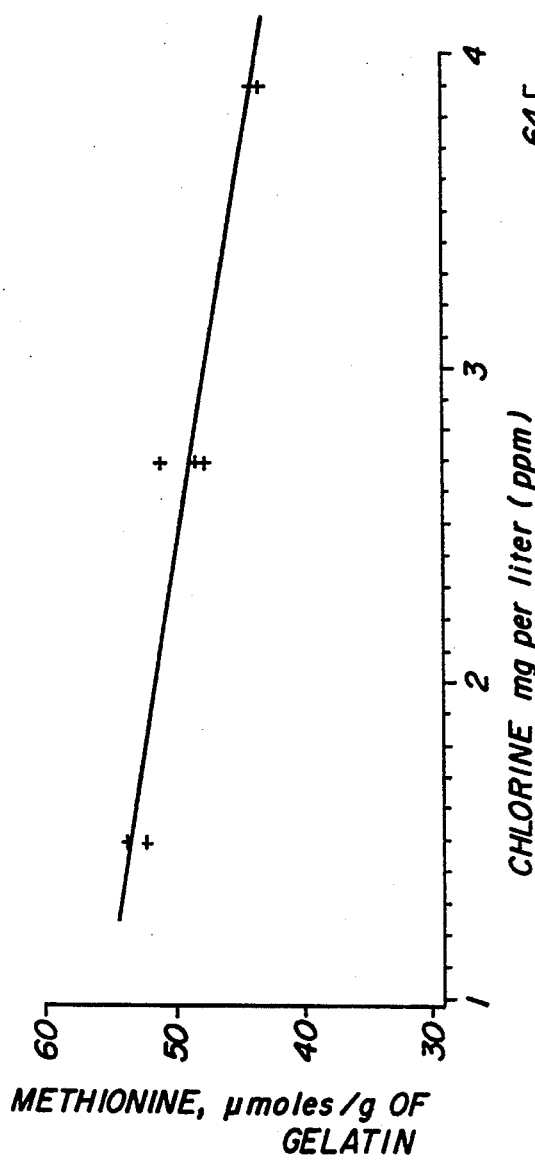
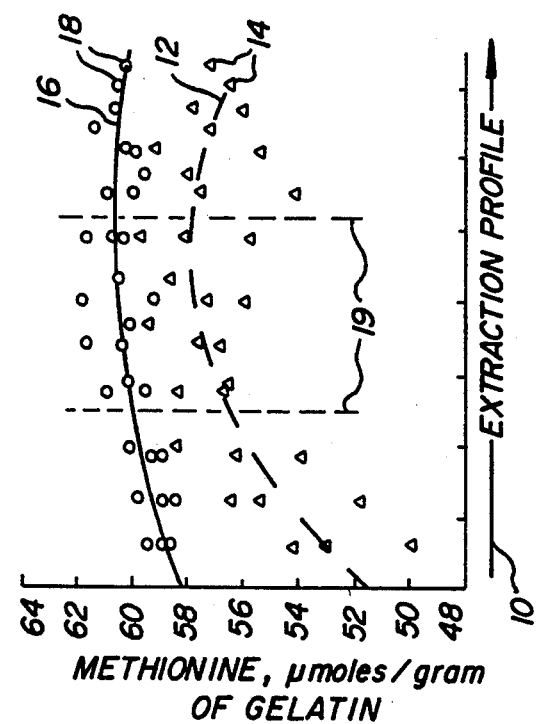
Fig. 3
Fig. 4

CONTROL OF METHIONINE CONTENT IN PHOTOGRAPHIC GRADE GELATIN

This is a continuation of application Ser. No. 07/849,483, filed on Mar. 11, 1992, now abandoned.

FIELD OF THE INVENTION

The invention relates to processes for the preparation of high grade gelatin useful in photography.

BACKGROUND OF THE INVENTION

Light-sensitive emulsions used in the photographic art are typically prepared from a discrete phase, known as grains, containing a light-sensitive component such as silver bromide and a continuous phase containing a peptizer and a binder. The peptizer is introduced into the emulsion during precipitation of the light sensitive component to prevent coalescence or flocculation. Preferred peptizers are gelatin, i.e., alkali-treated gelatin (cattle bone or hide gelatin) or acid-treated gelatin (pigskin gelatin), and gelatin derivatives, i.e., acetylated gelatin or phthalated gelatin.

The reproducible manufacture of gelatin is important because the characteristics of the gelatin are important to the photographic emulsion properties, in particular, the light-sensitivity of the emulsion, grain morphology, and latent image stability. It has been recognized as beneficial in the manufacture of gelatin to employ oxidizing treatments in order to destroy microorganisms and other harmful impurities. The use of oxidants such as hydrogen peroxide was suggested by Sheppard (S. E. Sheppard, Great Britain Patent No. 245,456) for the elimination of various impurities in the gelatin, and is similarly mentioned more recently by F. J. Moll, *J. Photog. Sci.* 37, 14 (1989).

Methionine is a component of gelatin and the control of its content is an important factor in the reproducible manufacture of gelatin. However, methionine oxidizes readily to methionine sulfoxide in the presence of oxidants such as hydrogen peroxide, sodium peroxide and hypochlorite as determined by Pouradier and Rondeau (*J. Photog. Sci.* 16, 68 (1968)). The methionine content of the gelatin is thereby altered by the prescribed oxidation treatment.

Maskasky in U.S. Pat. No. 4,713,320 demonstrated that oxidation of the methionine (thereby reducing methionine content) in gelatin used in a tabular grain emulsion will dramatically alter the grain morphology, thickness and rod content. Fox and Holden in U.S. Pat. No. 4,713,320 describe photographic gelatins with enhanced levels of methionine. The methionine level is an important parameter in the preparation of photographic grade gelatin. It is therefore desirable for a manufacturer to be able to control the methionine content of the gelatin.

SUMMARY OF THE INVENTION

It is the object of the present invention to provide a method for reducing variability in methionine levels in photographic gelatin during the washing and extraction of ossein stock. It is a further object of this invention to control overall methionine variability in gelatin from one ossein lot to the next.

One aspect of the present invention is directed to a process for preparing photographic grade gelatin with controlled methionine content by controlling the amount of oxidant present during processing of bone stock into gelatin. It is desirable to restrict the range of oxidant to less than 220 meq per 100 kg bone stock.

In preferred embodiments, the range of oxidant around an aim value can be controlled by controlling the level and range of the oxidant in the processing water which comes in contact with the ossein or gelatin. In other preferred embodiments, the level and range of oxidant is controlled by controlling the volume of water used during processing, particularly during washing of the bone stock. The total process water volume is preferably less than 30 kg of water per kg of bone and more preferably less than 25 kg of water per kg bone.

In other preferred embodiments, the oxidant is minimized or eliminated. Oxidant concentration can be minimized or eliminated by subjecting the process waters to a purification step, such as filtration through activated carbon. The oxidant can be minimized by further decreasing the volume of process water or by using known purification techniques to remove the oxidant from the process water supply. Alternate water supplies free of oxidant can be substituted for the oxidant-containing process water in some or all of the processing steps.

As expected lowering oxidant level in process waters leads to less oxidation of methionine in the gelatin extracted. However, by controlling oxidant at lower levels, we have also discovered an unexpected reduction in the difference between the lower methionine levels in the early extracts and the higher methionine levels in the latter extracts during the extraction of the gelatin from the ossein.

To obtain reproducible emulsion properties, the methionine content of the gelatin used as a peptizer is controlled preferably to within a total range of 4 $\mu$moles methionine per gram of gelatin or less and more preferably to within a total range of 3 $\mu$moles methionine per gram of gelatin or less. In preferred embodiments, reproducible methionine content is obtained by controlling the volume and/or the concentration of the undesired oxidant in the process water during processing of bone stock into gelatin.

A variation in methionine content is observed in the gelatin obtained from the successive extraction of ossein. Typically, multiple extractions are performed on a single batch of ossein with increasing temperature for each subsequent extraction. It is an advantage of the present invention that the excessive variation in methionine content throughout successive extractions is reduced. This allows a greater percentage of the extracted gelatin to fall around a mean within a desirably tight methionine specification, thus permitting it to be used in a high value application like emulsion making. In a preferred embodiment, controlled methionine levels are obtained by selectively blending extracts from that portion of the extraction profile in which methionine is most uniform.

In another aspect of the present invention, a method is provided for determining methionine concentration in gelatin. Gelatin is hydrolyzed to its constituent amino acids under inert atmosphere using methanesulfonic acid, whereby methionine is not oxidized or converted to methionine sulfoxide. The constituent amino acids are separated by high performance liquid chromatography and the eluted amino acids are complexed with ninhydrin. Measuring the absorbance of the ninhydrin complex provides information for calculating the methionine content of the gelatin.

Practice of the present invention provides a gelatin of controlled and reproducible methionine content. Reduced extraction-to-extraction and batch-to-batch variation of methionine in gelatin eliminates or reduces the need to perform time consuming or expensive analysis of each gelatin extraction.

BRIEF DESCRIPTION OF THE DRAWING

In the Drawing;

FIG. 3 is a graph of methionine content ($\mu$mole methionine/g gelatin) v. chlorine concentration (ppm); and FIG. 4 is a graph of methionine content ($\mu$mole methionine/g gelatin) as a function of the extraction profile.

DESCRIPTION OF THE PREFERRED EMBODIMENT

The present invention modifies the gelatin manufacturing process to produce a controllable and reproducible methionine content throughout the gelatin-making process within each process batch and from one process batch to the next. The present invention further permits control of the manufacturing process to obtain methionine levels within certain narrow limits. Oxidants, as that term is used herein, refers to species in the process waters that result in unintentional and variable oxidation. It is recognized that intentional and controlled oxidation could also be a part of the manufacturing process.

The sensitivity of a photographic emulsion usually changes when grain size or shape changes and this in turn alters the particle surface area of a mole of emulsion, expressed in $m^2$/mole. For a particular photographic emulsion with grains having a defined surface area per mole, a specific level of chemical sensitizer or dye is usually found to give the optimal response. If the emulsion area is changed, the prescribed amount of sensitizer or dye may no longer give the optimal response. During manufacturing, it is desirable for a given emulsion type to respond the same way to sensitization each time it is made.

Figure 1:
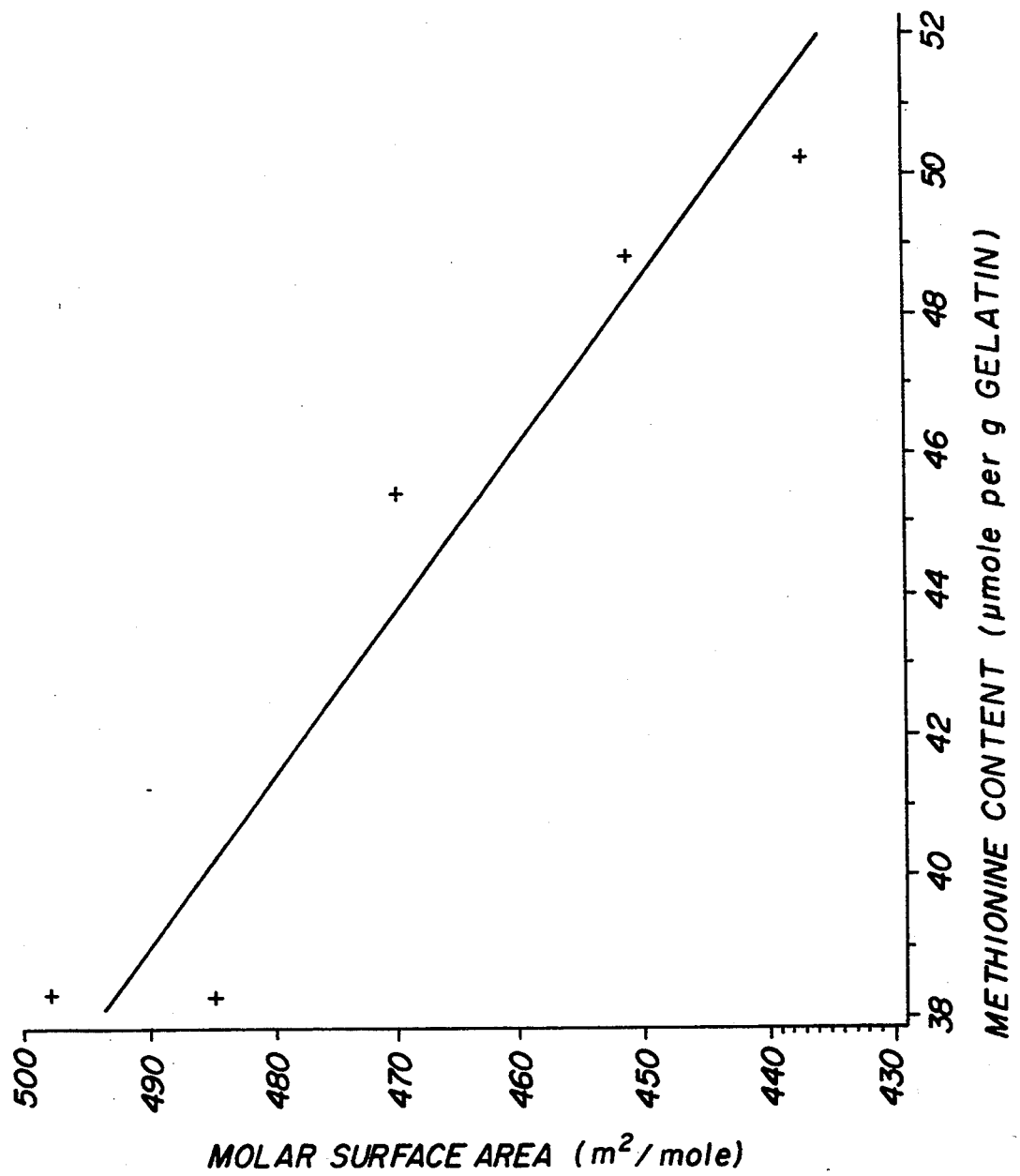
FIG. 1 is a graph of molar surface area of the emulsion ($m^2$/mole) v. methionine content ($\mu$mole methionine/g gelatin)

FIG. 1 illustrates the dramatic change in molar surface area when a specific emulsion is made in gelatins with varying amounts of methionine. In this particular case, the emulsion contains tabular AgBrI grains. A typical batch-to-batch variational range of 38–50 $\mu$mole methionine/g gelatin results in a 435–500 $m^2$/moles range in the emulsion's surface area. Variations in emulsion area such as those shown in FIG. 1 could require re-establishing the optimum sensitizing conditions when each new batch of gelatin is used. The need for reoptimization is costly and undesirable.

Gelatin is derived from animal protein, typically animal hides and bone. Of all the amino acids making up gelatin, methionine is the principal source of divalent sulfur atoms. Such sulfur sites have been shown to have a high affinity for silver halide grain surfaces. Thus, methionine in gelatin used in emulsion nucleation and grain growth has a strong influence on the properties of that emulsion.

Figure 2:
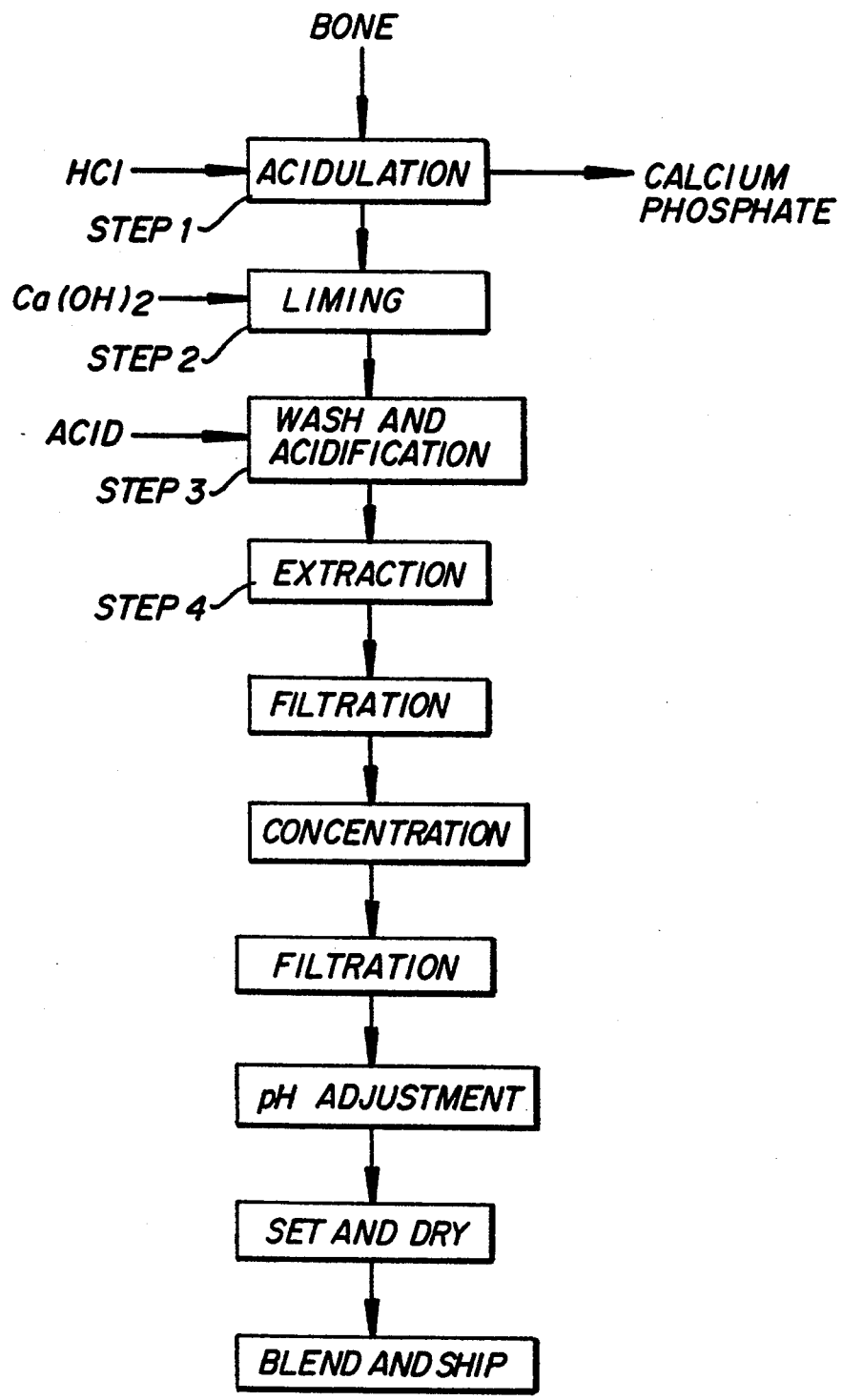
FIG. 2 is a flow diagram illustrating the general processing steps in the manufacture of gelatin.

Gelatin can be prepared by any conventional process used in the preparation of gelatin with the incorporation of one or more features of the present invention as discussed herein. FIG. 2 is a flow diagram of a typical process for making gelatin. Crushed and dried bone stock is acidulated with dilute aqueous HCl to demineralize the bone (steps 1 of FIG. 2), and then limed with aqueous calcium hydroxide for 7–12 weeks (steps 2 of FIG. 2). After liming, the demineralized bone (ossein) is washed with neutral water for 1–2 days (Post-lime wash of steps 3 of FIG. 2) and then allowed to sit in a dilute acidic bath to further lower the pH of the ossein (acidification steps of steps 3 of FIG. 2). The limed and washed ossein is repeatedly extracted with neutral water at elevated temperatures in order to obtain the gelatin (steps 4 of FIG. 2). The extracts are filtered, dried, and ground in a number of subsequent steps as illustrated in FIG. 2 to obtain a granular gelatin that is blended for use in the preparation of photographic emulsions.

Crucial to the control of methionine levels in gelatin is the development of a reliable method for determination of the composition of active methionine and its photographically inactive oxidation product, methionine sulfoxide. The commonly used practice of hydrolyzing proteins into their component amino acids with 6N HCl at 110° C., followed by the high-performance chromatography (HPLC) separation of the amino acids in the hydrolyzates is unsuitable for quantifying the level of unoxidized methionine. Under these conditions, methionine can be at least partially oxidized to methionine sulfoxide. Under these same hydrolysis conditions, methionine sulfoxide can also be reduced to methionine. The addition of 2-mercaptoethanol to the 6N HCl prevents the oxidation of methionine but quantitatively reduces methionine sulfoxide to methionine, resulting in the over-prediction of the true methionine level in gelatin. Another common hydrolysis procedure uses a strongly oxidizing acid such as performic acid. This results in the complete oxidation of methionine and methionine sulfoxide to methionine sulfone. This method is also unable to determine the methionine component in gelatin.

Methionine concentration is determined in the present invention using a novel adaptation of previously reported amino acid analysis procedures. Problems stemming from the facile interconversions between methionine and methionine sulfoxide during hydrolysis are overcome by hydrolysis in 4N methanesulfonic acid which has been thoroughly degassed to remove oxygen. The amino acids are separated by HPLC, followed by postcolumn derivatization with ninhydrin.

In this procedure, gelatin samples are hydrolyzed for 18.0 hours at 110° C. under argon using degassed 4N methanesulfonic acid. After hydrolysis, the hydrolyzates are adjusted to a pH of 2.2 with NaOH and then quantitatively adjusted to a final weight of 50 g with 0.2N sodium citrate buffer (pH 2.2). Methionine and methionine sulfoxide levels are measured in these hydrolyzates using HPLC in the cationic exchange mode. Samples are injected onto the HPLC column. The amino acids TABLE 1a

| time (min) | eluent $A^b$ (%) | eluent $B^c$ (%) | eluent $C^d$ (%) |
|---|---|---|---|
| 0.0 | 100 | 0 | 0 |
| 10.00 | 100 | 0 | 0 |
| 52.00 | 25 | 75 | 0 |
| 53.00 | 0 | 80 | 20 |
| 54.00 | 0 | 0 | 100 |
| 59.00 | 0 | 0 | 100 |
| 60.00 | 100 | 0 | 0 |

TABLE 1a-continued

| time (min) | eluent A$^b$ (%) | eluent B$^c$ (%) | eluent C$^d$ (%) |
| --- | --- | --- | --- |
| 90.00 | 100 | 0 | 0 | a flow rate = 0.400 ml/min
$^b$0.2 N Sodium Buffer, pH 2.98 (Pickering Laboratories, Inc.)
$^c$1.0 N Sodium Eluent, pH 7.40 (Pickering Laboratories, Inc.)
$^d$0.2 N Sodium Column Regenerate (Pickering Laboratories, Inc.)
$^e$Sodium column, 4.6 mm × 250 mm (Waters, Division of Millipore, P/N 80002)
$^f$Trione ninhydrin reagent (registered trademark of Pickering Laboratories, Inc.)

are eluted using buffers of increasing pH and ionic strength. Eluent conditions are described in detail in Table 1. The effluent from the column is mixed with ninhydrin reagent$^f$ (delivered at 0.4–0.5 mL/min) in a postcolunm reaction coil at 130° C. A detector measures the absorbance of the colored ninhydrin complex at 570 nm. Standards of known concentration are run to verify retention position and determine concentration/response ratios. Methionine sulfoxide, methionine, and total methionine (methionine+methionine sulfoxide) are determined in micromoles per gram of dry gelatin. The oxidation level is reported as a percent (methionine sulfoxide/total methione × 100).

The variability of methionine in the gelatin is directly related to the exposure of ossein to variable levels of oxidants such as hypochlorite salts, chlorine, hydrogen peroxide, permanganate, ozone or other oxidants during processing. Such oxidants are often added in gelatin-making processes as water-treatment agents for control of microbial growth or for oxidation of metallic impurities to higher oxidation states which are less soluble. These oxidants are "undesirable" in that their secondary effect, the uncontrolled oxidation of methionine to methionine sulfoxide, is not desired. The present invention appreciates that even at extremely low concentrations, variability of such oxidants in process water can produce unwanted variability in methionine levels in the final gelatin. For gelatin used in tabular grain emulsion precipitation, methionine must be controlled to within a relatively narrow range around some median value. The present invention includes methods for control of methionine at predetermined and reproducible levels.

The variability of methionine levels in gelatin has been shown to be related to the undesired variability in oxidant concentration in the process water. A significant oxidant in the gelatin-making process is often chlorine or hypochlorite salts which are added to the process water to destroy or prevent growth of biological impurities and to oxidize more soluble metal ions to a higher oxidation state to facilitate their removal from the water. In the experimental results depicted graphically in FIG. 3, the ratio of post-lime wash water volume (see, post-lime wash steps of steps 3, FIG. 2) to ossein weight was constant and the effect of chlorine concentration on the methionine level is clearly demonstrated. A change in the chlorine level of 1 ppm in post-limed wash water produced a 4.3 μmole change in the methionine level per gram of gelatin.

A second important variable in the gelatin-making process is the volume of process water used per kg of bone stock. FIG. 4 shows the methionine level (μmole methionine per gram of gelatin) as a function of the extraction profile for three batches of ossein washed with a high post-lime wash water volume (steps 3, FIG. 2) and three batches of ossein washed with a low post-lime wash water volume (steps 3, FIG. 2). By "extraction profile", it is meant the consecutive extraction treatments of the limed and washed ossein, with subsequent steps occurring in the direction indicated by arrow 10 in FIG. 4 (steps 4, FIG. 2). Multiple extractions are performed on a single batch of ossein with increasing temperature for each subsequent extraction. The "high wash water volume process" used 57 kg water per kg of dry bone stock in the post-lime wash step. The "low wash water volume process" used 23 kg water per kg of dry bone stock in the post-lime wash step. The oxidant concentration in all process water was kept constant in both high and low wash water volume processes.

A lower curve 12 is drawn through data points designated by triangles 14 to designate the methionine levels across the extraction profile of ossein subjected to a high wash water volume process. An upper curve 16 is drawn through data points designated by circles 18 to indicate the same for the low wash water volume process. It is clear that at all points during the extraction, the methionine level was higher for the low wash water volume process, that is, methionine levels increased when process wash water volume decreased. A higher methionine level for the low wash water volume process means that less of the methionine is oxidized to methionine sulfoxide.

It was further determined that the methionine content of the gelatin made using standard manufacturing procedures varied substantially throughout the extraction profile. This is apparent from observing the shape of curves 12 and 16. Any deviation of the slope of these curves from zero indicates variation in the methionine content from one extraction step to the next. The deviation of the slope of curve 12 from zero for the high volume process is particularly noticeable. Methionine levels are at their lowest in the first third of the extraction profile curve and reach a maximum near completion of two-thirds of the extraction steps. In subsequent extractions, the methionine level again begins to decline. In contrast, curve 16 for the low volume process is nearly flat across the entire extraction profile.

Table 2 shows the exposure level of ossein to oxidant in process water used in gelatin manufacture along with the corresponding methionine ranges in the resultant gelatin. If limits on the total range of methionine variability of 4 μmole methionine/gram gelatin are imposed, then the entire contents of the extraction profile designated by curve 16 (experiment 3, Table 2) meet this criterion. However, such a 4 μmole range would require that only a narrow range within dotted lines 19 of the extraction profile of curve 12 (experiment 2, Table 2) may be used. If the acceptable total range is narrowed to a more desirable 3.0 μmole methionine/gram gelatin, then only a selected blending range (within dotted lines 19) within the extraction profile of curve 16 (experiment 4 of Table 2) meets the criterion. With the higher batch to batch variability as well as the higher variation with extraction profile, it would be difficult to pick in advance any portion of the extraction profile of curve 12 that would meet the more restrictive criterion of 3.0 μmole methionine/gram gelatin.

Referring to the data provided in Table 2, to control methionine to within a total range of 2.6 μmoles methionine per gram of gelatin, the total range of oxidant must be less than 155 meq per 100 kg dry bone stock. In addition, process water volume in the wash step must be below 23 kg/kg bone and selected blending is required. If, however, the total range of allowable methionine increases to 4.0 μmole/gram gelatin, then the range of oxidant can increase to 390 meq/100 kg dry bone stock, using selective blending and water volumes below 57 kg/100 kg bone. Generally, one can show that keeping the oxidant range below 220 meq/100 kg bone, keeping the wash water volume below 23 kg/100 kg bone and using selective blending will reduce the range of methionine to

TABLE 2

| Experiment | chlorine range (meq/100 kg bone) | Methionine range (μmole/g gelatin) |
| --- | --- | --- |
| 1 Non-selective Blend Range High Volume Water* | 390 | 9.9 |
| 2 Selective Blend Range High Volume Water | 390 | 4.0 |
| 3 Non-selective Blend Range Low Volume Water[b] | 155 | 3.5 |
| 4 Selective Blend Range Low Volume Water | 155 | 2.6 |

[a]57 kg water/kg bone in wash step
[b]23 kg water/kg bone in wash step less than 3.0 μmoles methionine/gram gelatin.

In some cases, it may be desirable to minimize or eliminate the oxidant from the process water. This can be accomplished by reducing the process water volume even further or by using a standard technique to remove the oxidant prior to use in the gelatin-making process. Examples of such methods are: absorption of the oxidant by activated carbon; treatment with sodium bisulfite or other chemical reducing agents; or in the case of chlorine or hypochlorite, by exposure to ultraviolet irradiation, aeration or sonication. Alternate water supplies that are free from undesired oxidants can be introduced in all or some of the processing steps shown in FIG. 2.

From the above description, it is clean that by controlling the range of oxidant concentration in the processing water and the volume of process water for a given weight of ossein and by restricting the range of extraction profile used in blending, it is possible to restrict methionine content of the resulting gelatin blends to the narrow range needed for the reproducible manufacture of photographic emulsion. Gelatin with uniform methionine content may be used in any of the normal uses of gelatin, but it would be most useful in the precipitation of all silver halide emulsions and especially beneficial in preparing tabular emulsions in a reproducible manner.

What is claimed is:

1. A process for preparing photographic grade gelatin from bone stock in which the variability of the methionine content of said gelatin is regulated to within a total range of 4 μmoles of methionine per gram of gelatin, said process comprising the steps of:
   acidulating the bone stock,
   liming the acidulated bone stock,
   washing the limed bone stock, and
   extracting gelatin from the washed bone stock; said process including exposure of said gelatin to an oxidant during at least one of said processing steps; and said process being characterized in that the variability of the methionine content of said gelatin is regulated to within said total range of 4 μmoles of methionine per gram of gelatin by controlling the extent to which said gelatin is exposed to said oxidant during said at least one processing step to a range of oxidant which provides said range of methionine content.

2. A process as claimed in claim 1, wherein said washing step utilizes an amount of water of less than 57 kg per kg of bone.

3. A process as claimed in claim 1, wherein said washing step utilizes an amount of water of less than 23 kg per kg of bone.

4. A process as claimed in claim 1, wherein oxidant-containing water is utilized in said at least one processing step and controlling the extent of exposure of said gelatin to said oxidant is achieved by controlling the volume of said oxidant-containing water.

5. A process as claimed in claim 1, wherein said oxidant is selected from the group consisting of hypochlorite salts, chlorine, hydrogen peroxide, peroxide salts, peroxy acids and permanganate salts.

* * * * *